(12) United States Patent
Saharan (10) Patent No.: US 9,249,188 B2
(45) Date of Patent: Feb. 2, 2016

(54) MAMMALIAN COLOSTRUM DERIVED NANOPEPTIDES FOR BROADSPECTRUM VIRAL AND RECURRENT INFECTIONS WITH A METHOD OF ISOLATION THEREOF

(71) Applicant: Pawan Saharan, Maharashtra (IN)

(72) Inventor: Pawan Saharan, Maharashtra (IN)

( * ) Notice: Subject to any disclaimer, the term of this patent is extended or adjusted under 35 U.S.C. 154(b) by 75 days.

(21) Appl. No.: 13/845,577

(22) Filed: Mar. 18, 2013

(65) Prior Publication Data

US 2013/0274177 A1     Oct. 17, 2013

Related U.S. Application Data

(62) Division of application No. 13/142,327, filed as application No. PCT/IN2009/000749 on Dec. 29, 2009, now Pat. No. 8,518,454.

(30) Foreign Application Priority Data

Dec. 27, 2008   (IN) .................. 1353/MUM/2008

(51) Int. Cl.
| | |
|---|---|
| A61K 38/00 | (2006.01) |
| A01N 37/18 | (2006.01) |
| A61P 31/18 | (2006.01) |
| A61K 38/10 | (2006.01) |
| A61K 38/08 | (2006.01) |
| C07K 7/08 | (2006.01) |
| A61K 35/20 | (2006.01) |
| C07K 7/06 | (2006.01) |

(52) U.S. Cl.
CPC . *C07K 7/08* (2013.01); *A61K 35/20* (2013.01); *A61K 38/08* (2013.01); *A61K 38/10* (2013.01); *C07K 7/06* (2013.01)

(58) Field of Classification Search
CPC .................................... C07K 7/08; C07K 7/06
See application file for complete search history.

(56) References Cited

U.S. PATENT DOCUMENTS

| 5,683,878 | A | 11/1997 | Ellmeier et al. |
| 2002/0127279 | A1 | 9/2002 | Matthews |
| 2003/0103968 | A1* | 6/2003 | Amelsberg et al. ........ 424/138.1 |
| 2005/0175597 | A1 | 8/2005 | Rawlin et al. |
| 2007/0212367 | A1* | 9/2007 | Keech ........................ 424/185.1 |

FOREIGN PATENT DOCUMENTS

| KR | 20020024902 A | 4/2002 |
| WO | 01/55199 A1 | 8/2001 |
| WO | 01/62785 A2 | 8/2001 |
| WO | 2005/081628 A2 | 9/2005 |

OTHER PUBLICATIONS

Blake, Bovine Colostrum, The Forgotten Miracle, Journal of the American Holistic Veterinary Medical Association Jul. 1999, vol. 18, No. 2, pp. 39-40.*
Fonterra Co-operative Group Ltd, Colostrum and Stolle Sales Get a Boost from SARS, 2003.*
Veracity, Colostrum is a proven, effective immune system booster, Natural News, 2005.*
Hong, S.Y. and Qin, Z.B.; "Inhibitor of Binding 3" XP002586928, Aug. 2, 2005, retrieved from EBI Database accession No. Q4JQP9.
Struff W.G. et al.; "Bovine colostrum as a biologic in clinical medicine: a review—Part II: clinical studies"; Int. Journal of Clinical Pharmacology and Therapeutics, vol. 46, No. 5, pp. 211-225, May 1, 2008; XP009150270, ISSN: 0946-1965.
Bocci V., Von Bremen K., Corradeschi F., Luzzi E., Paulesu L.; "Colostrum stimulates the lymphoid tissue providing benefits in aged or immunodeficient people"; Journal Biology Regul Homeost Agents, Oct.-Dec.; 5(4):121-4; 1991; abstract only, full-text unavailable.
Oda, S. et al.; "Insulin-like growth factor-I, GH, insulin and glucagon concentrations in bovine colostrum and in plasma of dairy cows and neonatal calves around parturition"; Comp. Biochem. Physiol.; vol. 94A, No. 4, pp. 805-808, 1989.
Bhora, F.Y. et al. "Effect of growth factors on cell proliferation and epithelialization in human skin", Journal of surgical Research; vol. 59, pp. 236-244, 1995.
Examination report of corresponding European patent application 09827010.1, issued on Mar. 20, 2013.

* cited by examiner

*Primary Examiner* — Karlheinz R Skowronek
*Assistant Examiner* — Sergio Coffa
(74) *Attorney, Agent, or Firm* — Nath, Goldberg & Meyer; Tanya E. Harkins (57) ABSTRACT

The present Invention relates to nanopeptides isolated from mammalian colostrums with vaccine like antiviral and immunodulator activity via building body's own immune system and attachment inhibition on the cell surface receptors.

9 Claims, 10 Drawing Sheets

MAMMALIAN COLOSTRUM DERIVED NANOPEPTIDES FOR BROADSPECTRUM VIRAL AND RECURRENT INFECTIONS WITH A METHOD OF ISOLATION THEREOF

This is a Divisional Application of U.S. patent application Ser. No. 13/142,327, filed Jun. 27, 2011, an application filed as a national stage under 371 of Application No. PCT/IN2009/000749 filed Dec. 29, 2009 and claiming benefit from Indian Application No. 1353/MUM/2008, filed Dec. 27, 2008, the content of each of which is hereby incorporated by reference in its entirety.

FIELD OF THE INVENTION

The present invention relates to nanopeptides isolated from mammalian colostrum with vaccine like antiviral and immunodulator activity via building body's own immune system and attachment inhibition on the cell surface receptors.

The Sequence Listing submitted in text format (.txt) filed herewith, named "seq.txt", (created on Dec. 27, 2008), is incorporated herein by reference.

BACKGROUND OF THE INVENTION

Colostrum is the pre-milk substance produced from the mother's breasts of all mammals during the first 24 hrs of lactation typically first 3 milks. Colostrum has been known as an immune booster since time immemorial. Colostrum triggers at least 50 processes in the newborn, including transferring all immune factors and the entire memory from mother's own immune system. Bovine colostrum is up to 40 times higher than human colostrums in immune factors including nanoinformational peptides, Proline Rich Polypeptides, immunoglobulins, cytokines, interferon, lactoferrin and transfer factor. They are produced by T-lymphocytes and can transfer the ability to recognize a pathogen to naïve cells. However, no one till date has been able to isolate active ingredients especially nano informational low molecular weight nanopeptides and formulate a product that has the same effect that mother's first 3 milk, after the birth of child.

"Colostrum stimulates the lymphoid tissue providing benefits in aged or immuno-deficient people" . . . Drs. Bocci, Bremen, Corradeschi, Luzzi and Paulesu; Journal Biology.

"Researchers reported that colostrum stimulates maturation of B Lymphocytes (type of white blood cell) and primes them for production of antibodies, enhances growth and differentiation of white blood cells. Similar activity in cow and human colostrum can also activate Macrophages" . . . Dr. M. Julius, McGill University, Montreal: Science News.

"Bovine colostrum contains high levels of growth factors that promote normal cell growth and DNA synthesis" . . . Drs. Oda, Shinnichi, et. al.;

Comparative Biochemical Physiology. "Drs. suggest that an important role for growth factors is in promoting wound healing. Accelerated healing is possible for treatment with trauma and surgical wounds" . . . Drs. Bhora, et. al.; Journal. Surg. Res.

US 20070212367—This patent application discloses an immunologically active PRP isolated from mammalian colostral fluids for treatment of viral and non-viral diseases, a method and a system for processing mammalian colostral fluids and a pharmaceutical formulation.

Colostrum as such contains hundreds of small peptides which serve numerous purposes. Their segregation and isolation will facilitate gathering of further information with regard to their individual function and help formulate specific and targeted therapies for numerous diseases that are cured by colostrum. Studies have documented the presence of number of bioactive peptides but no mention has been made of the use of these peptides fragments, their specific sequence or information regarding their isolation. The peptides are extremely sensitive to temperature, pH, stress and shear factors which posse several difficulties in their isolation and preserving their biological activity and method of collection of colostrum so as to deliver it to the required patient by maintaining its full biological activity.

The present invention addresses these shortcomings by providing isolated nano-peptides from colostrum, their method of isolation and therapeutic uses of the isolated nano-peptide fragments.

SUMMARY OF THE INVENTION

One embodiment of the present invention provides for a formulation comprising peptides isolated from mammalian colostrum having sequences as recited in SEQ ID 1-8 hereinafter referred to as peptides of Radha 108 series, wherein the peptides function to modulate cell immunity and provide attachment inhibition for foreign antigen/viruses on cell surface receptors along with crossing BBB (blood brain barrier) and treating host of diseases in the brain Colostrum is the pre-milk substance produced from the mother's breasts of all mammals during the first 24 hrs of lactation typically first 3 milks. In one embodiment, colostrum used in the present invention is of bovine origin. Bovine colostrum has 40 times higher immune factors than human colostrum and has the ability to cure a number of viral, immune and auto-immune disorders.

In another embodiment, there is provided a method of treatment of immune related disorders including autoimmune disorders the method comprising of administering a patient suffering from such disorders a therapeutically effective amount of formulation comprising the peptides of SEQ ID 108.

In yet another embodiment, there is provided a method of treatment of Acquired Immune Deficiency Syndrome or AIDS the method comprising administering a patient suffering from AIDS, a therapeutically effective amount of formulation comprising the peptides of SEQ ID 1-8.

The formulation can be provided in a liquid, powder gel and any other pharmaceutical delivery forms. It can be administered orally, intravenously or by means of dermal patch for adsorption through skin.

The present invention is illustrated with the help of accompanying drawings and detailed description and examples given below. The drawings and example are for explanation and clarity purpose and do not in any way limit the scope of the invention being defined by the appended claims and equivalents thereof. The foregoing aspects and advantages of the present invention will become more clear and appreciated by the detailed description and examples.

A BRIEF DESCRIPTION OF THE INVENTION

The present invention relates to peptides isolated from colostrum, their innovative methods of collection, transport, storage, isolation and therapeutic uses of the same.

One embodiment of the present invention relates to peptides isolated from mammalian colostrum. The mammal can be bovine for example cow, goat, buffalo or any other suitable mammal. In one preferred embodiment of the present invention, the isolated peptides are obtained from lactating cows and buffaloes in particular. The peptides are short chain amino acid sequences which are fragile sensitive to temperature, pH and shear stress and difficult to isolate. These peptides are in a segregated form. They are not binded by any other molecule. The isolated peptides comprise of the group of SEQ ID (1-8) and will be hereinafter referred to as Radha 108. Peptides of Radha 108 and do not coagulate being low in molecular weight. They are isolated from fat free whey obtained from the colostrum. The peptides of Radha 108 have a molecular weight in the range of 826 to 2990 kDa.

According to one embodiment of the present invention there is provided a method for collection and processing colostrum and isolating small amino acid sequences comprising of SEQ ID (1-8) the method comprising the steps of, separating fat, cheese and colostrum whey, passing the whey through a series of filters to remove suspended solids and reduce microbial load followed by ultra and nano filters to obtain a protein fraction having a molecular weight of less than 10000 kDa, specifically below 3500 kDa wherein the filtration is done at a low pressure, minimal shear and temperature to preserve the Radha 108 nano peptides. Even the pumping means used to pump the liquid through the system consist of pumps with low rpm. In one embodiment, the nano and ultra filters are designed to operate at a low shear and pressure of less than 5 Kg/cmsq. In another preferred embodiment, the filters are designed to operate in the range of 0.5 kg/cmsq to 4 kg/cmsq. In yet another preferred embodiment, the filters are designed to operate at a pressure range between 0.5 kg/cmsq and 2.0 kg/cmsq. Nano and ultra filtration of proteins at such low pressures is virtually unheard off due to practical difficulties in obtaining effective amounts of protein within acceptable time limits. The present invention thus overcomes the problem of prior art with regard to isolation and separation of small peptide molecules.

Colostrum is collected after delivery from mammal, and cooled to a temperature in the range of −20 deg C. within 3 hours to preserve the biological activity of Radha 108 series nano peptides. Care is taken to preserve these sensitive peptides right from the collection stage by provisions of special custom made non reactive plastic bags which help in the non reactive aseptic collection of milk from the calf. The handlers and collector of the milk are to be provided special instruction for the collection in order to avoid drastic changed to the sensitive peptides so that they don't loose their activity. The colostrum is then gradually thawed at room temperature over night to bring the temperature to 4 to 5 deg C., and pumped to a cream separator for removal of fats at 4000 RPM at 45 deg C. It is then pasteurized by increasing the temperature to 72 deg C. for 15 sec followed by cooling to 48 deg C. The colostrum is then received into cheese vat and treated with enzyme Rennet for 45-60 min to form curd and whey. The whey is cooled and passed through a series of filters up to molecular exclusion nano and ultra-filtration at low pressure and temperature for separation to peptides having a molecular weight of less than 10000 kDa. After the process care is taken to adjust the pH and keep it constant in the range of pH 4 to pH 6 in order to avoid degradation and loss of biological activity of the peptides of Radha 108. The protein fraction containing peptides less than 10000 kDa In another embodiment of the present invention there is provided a method of treating Acquired Immune Deficiency Syndrome or AIDS, the method comprising administering a patient suffering from AIDS, a therapeutically effective amount of a formulation comprising peptides of SEQ ID 1-8.

The peptides of the present invention block receptors GP120, 160, 180, 41 and other cell receptor sites through which foreign antigen/virus enters the immune and other cell types. Topographically, these peptides are similar to virus size and when they dock on these receptor sites mimicking the virus/antigen, thereby limiting the entry of foreign infectious agents though competitive attachment inhibition. The product also has a vaccine like effect via providing memory to B Cells at stem cell level and preventing future outbreak of the disease.

In another embodiment of the present invention there is provided a method of treating swine flu in mammals, the method comprising administering a patient suffering from swine flu, a therapeutically effective amount of a formulation comprising peptides of Radha 108.

In another embodiment of the present invention there is provided a method of treating immune disorders including autoimmune disorders comprising administering a patient suffering from such disorders a pharmaceutically effective dosage/amount of formulation comprising peptides of Radha 108.

The immuno-modulatory action of peptides of Radha 108 takes place by stimulating the maturation of immature thymocytes into either helper or suppressor T cells, depending on the need of the body. Helper T cells present antigens (such as viral protein) to B lymphocytes, which produce antibodies to that antigen. Helper T cells also help produce memory T cells, which retain the memory of an antigen in order to expedite the production of antibodies in the event the antigen is re-encountered in the future creating vaccine like memory for the first time in history of use of colostrum. Suppressor T cells, on the other hand, deactivate other lymphocytes after an infection has been cleared to avoid damage to healthy tissues. Peptides of the present invention also promote the growth and differentiation of B cells in the response to an infection and the differentiation and maturation of macrophages and monocytes The activity of Natural Killer cells from Thymus gland via Radha 108 series of peptide that crosses BBB (Blood Brain Barrier), cytotoxic cells of the innate immune system, was increased up to 5 times by the peptides (Radha 108) of the present invention.

The peptides of the present invention are also known to modulate the cytokine system as well. It stimulates the production of a wide range of cytokines, including the pro-inflammatory cytokines tumor necrosis factor-alpha (TNF-$\alpha$) and interferon alfa and gamma (INF-$\gamma$) and anti-inflammatory cytokines interleukin (IL1, IL2, IL6, IL10, IL11, IL12) immuno-modulators.

The peptides of the present invention are small nanopeptides ranging between 800 to 3200 daltons and hence they are able to cross the blood brain barrier, and treat viral infections and neural disorders in brain via signaling Pituitary gland located in the brain. It also acts on the signaling pathways through Pituitary gland that sends signals to thymus in throat and stem cells in bone marrow, building body's own immune system naturally without the help of any other external medications.

According to another embodiment of the present invention there is provided a pharmaceutical formulation comprising the peptides of the present invention as an active pharmaceutical ingredient (API) and pharmaceutically acceptable carriers. Optionally, the formulation further comprises Proline Rich Polypeptides or PRP's commonly found in colostrum as additional active ingredient. The formulation is used for the treatment of wide range of diseases such as viral, bacterial, mycobacterium, fungal, parasitic, immune disorders including autoimmune disorders etc.

According to another embodiment of the present invention there is provided a method for treating a person suffering from immune related disorders the method comprising administering a the dose of formulation comprising of peptides of the present invention in the range of 2 ml to 5 ml in a spray form inside the mouth on buccal mucosa or on the any other surface of body-skin or nasal cavity (4 times a day).

According to another embodiment of the present invention the formulation can be applied topically or as a skin/transdermal patch or through the nasal or intravenous route.

The formulation of the present invention is known to cure around 108 disease which include AIDS, allergies, Alzheimer, Benign Prostatic Hyperplasia, Cancer, Hypertension, Lupus, Thrush, Autism, Perth's disease, Premenstrual syndrome and Endometriosis, Prion disease, Psoriasis, Sjogren's Syndrome, Spinal Muscular Atrophy, Thrombocytopenia, burns, infection insect bites, diaper rash, herpetic lesions, perther disease, Pharangitis, Porphyria, Raynaud's phenomenon, Sarcoidosis, Celiac disease, Chronic Pancytopenia, Crohn's disease, Diabetes type II, Fibromyalgia Rheumatic, Mononucleosis, Multiple Sclerosis, Rheumatoid Arthritis, Osteo Arthritis, Spinal Muscular Atrophy, Brown Recluse Spider Bite, Corneal Regeneration, diarrhea, Guillain Barre Syndrome, Hemolytic Anemia, Idiopathic Thrombocytopenia purpura, Myasthenia Gravis, lupus, tuberculosis, HIV, Hepatitis A&C, Rabies in Dogs, Acute Viral Infections, Dengue fever, Human Papilloma Virus, Parvo, Pharangitis, Rabies, SARS, Shingles, Viral Respiratory Infection, Plantar Warts, Colds and Flu, Lymphoma and Herpes Simplex I & II, wound healing, bone density building and skin elasticity, insulin like growth factors, Anti aging etc.

Additional health benefits from Radha 108 series include Anabolic, Anti Aging, Anti fungal, Anti-inflamatory, Anti-microbial, Assimilation, Athletic performance, body building, bone density, cytokine enhancement, digestion, epithelial growth factors, friendly flora enhancement, insulin like growth factors, immunity booster, immunoglobulin, interferon, interleukins, intestinal permeability, lactoferrin, MSM, Muscle toning, skin elasticity, stamina, transforming growth factors, wound healing and weight loss for obese.

The invention will now be described with the help of example provided herein which is meant only for the purpose of illustration and understanding and does not in any way limit the scope of the present invention.

Example

Pregnant cattle were identified from various heard through the Amul's Kheda district of Anand in Gujarat India through computerized record keeping systems of Amul Dairy. Colostrum obtained from the cattle soon after delivery was collected and stored in aseptic temperature controlled collection vessels at a temperature of 4 deg C. to preserve the biological activity of the peptides. It was further freezed to −20 deg C. till future processing. For separation of peptides of the present invention, colostrum was gradually thawed at room temperature over night to bring the temperature to 4 to 5 deg C. It was then pumped to the cream separator for removal of fats at 4000 RPM at 45 deg C. This was followed by pasteurization at a temperature of 72 deg C. for 15 sec followed by cooling at 48 deg C. and receiving the pasteurized colostrum into cheese vat. Enzyme Rennet was added to the cheese vat and allowed to react for 60 min after which the curd formed was separated from colostrum whey. The whey was cooled to 4 to 10 deg C. It was then passed through a series of filters to remove suspended solids and microbial load all the way up to molecular exclusion nano ultra-filtration for separation to peptides having molecular weight less than 10 kDa to obtain peptides of the present invention in a mixture along with Radha 108 series and PRP's present in the colostrum.

During process Difiltration is carried out by adding 10% purified water of total batch size. Presence of the peptides of SEQ ID 1-8 was verified using HPLC techniques.

Preservatives are added to the fraction obtained after ultrafiltration and pH is adjusted between 4 to 6. The formulation was provided in a spray form in order to test its efficacy in human trial.

The patients who were administered formulation comprising peptides of the present invention were neither exposed before nor were on any other drugs especially, anti-retroviral and antibiotics therapies at the time of administration of the drug. Thus, the formulation of the present invention can be effectively used as a standalone therapy.

WHO approved end points for assessing the therapeutic usage of formulation of the present invention were scientifically analyzed through the Indian Government sponsored and monitored study on 2 sets of patients at LTMMC and LTMG municipal tertiary care hospital in Sion, Mumbai with end point analysis for weight gain and clinical symptoms carried out the Sion Hospital and viralogical (viral load) and immunological (absolute CD4 count analysis) being done at two separate internationally recognized center (Institute of Immunoheamatology, Indian Council of Medical Research Institute in Mumbai and Metropolis Central Laboratory in Mumbai India having approval from USA pathological association and accreditation from NABL, Department of Science and Technology Government of India.

The statistical analysis of both these sets of studies were undertaken at the premier medical research institute in India; All India Institute of Medical Sciences New Delhi.

A. Initially, 50 participants were evaluated in the clinic once a week through the first 4 weeks of therapy, and then every 2 weeks for the remaining 8 weeks of the study. They were evaluated about clinical and physical symptoms via symptom assessment form, physical examination, side effect of treatment and compliance to the drug on follow up visits. Blood tests to measure CD4 cell count, HIV viral load, heamoglobin, white blood cell count, liver function test and renal function test were done at baseline and at end of 12 weeks study.

CD4 and CD8 cell count were analyzed via Flow Cytometry and Viral Load via Polymerase Chain Reaction at the beginning and at the end of 12 weeks.

Primary efficacy end points of study was the effect of this therapy on the markers of HIV disease including clinical symptoms and physical findings, weight gain/loss along with the general well being of the patients and HIV viral load and CD4 cell count, which showed consistently positive results in both the trials conducted since 2005 Onwards.

Weight Gain: Consistent weight gain was observed in all patients on follow-up visits, which was one of the primary end point (Table 1). The average weight gain after 12 weeks of treatment was 4.73 kg per patient, which is statistically highly significant (p<0.001).

TABLE 1 changes in mean weight after treatment

| Duration in weeks | Mean weight (N = 50) |
|---|---|
| basal | 50.48 ± 10.97 |
| 2 | 50.77 ± 11.26 |
| 3 | 51.38 ± 10.94 |
| 4 | 52.33 ± 10.73 |
| 6 | 53.89 ± 11.17 |
| 8 | 54.59 ± 10.89 |
| 10 | 55.44 ± 11.07 |
| 12 | 55.21 ± 9.42 |

Clinical parameters: All the clinical symptoms disappeared during the 12 weeks of treatment. These reductions are statistically significant (p<0.05).

Figure 1:
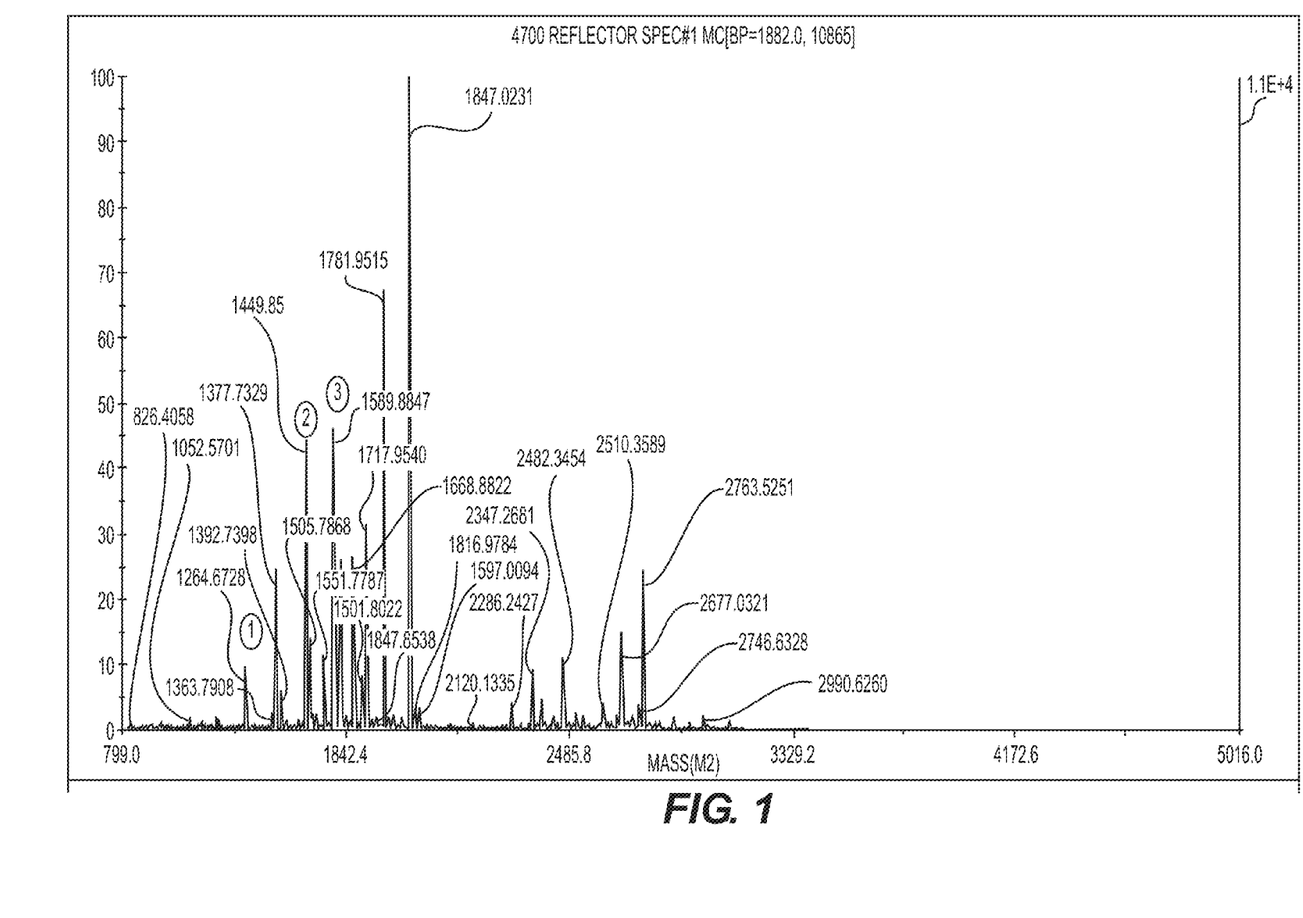
FIG. 1: Resolution of bovine colostrum sample used in the present invention through MS Spectra to give various protein fragments of different molecular weights.
Figure 2:
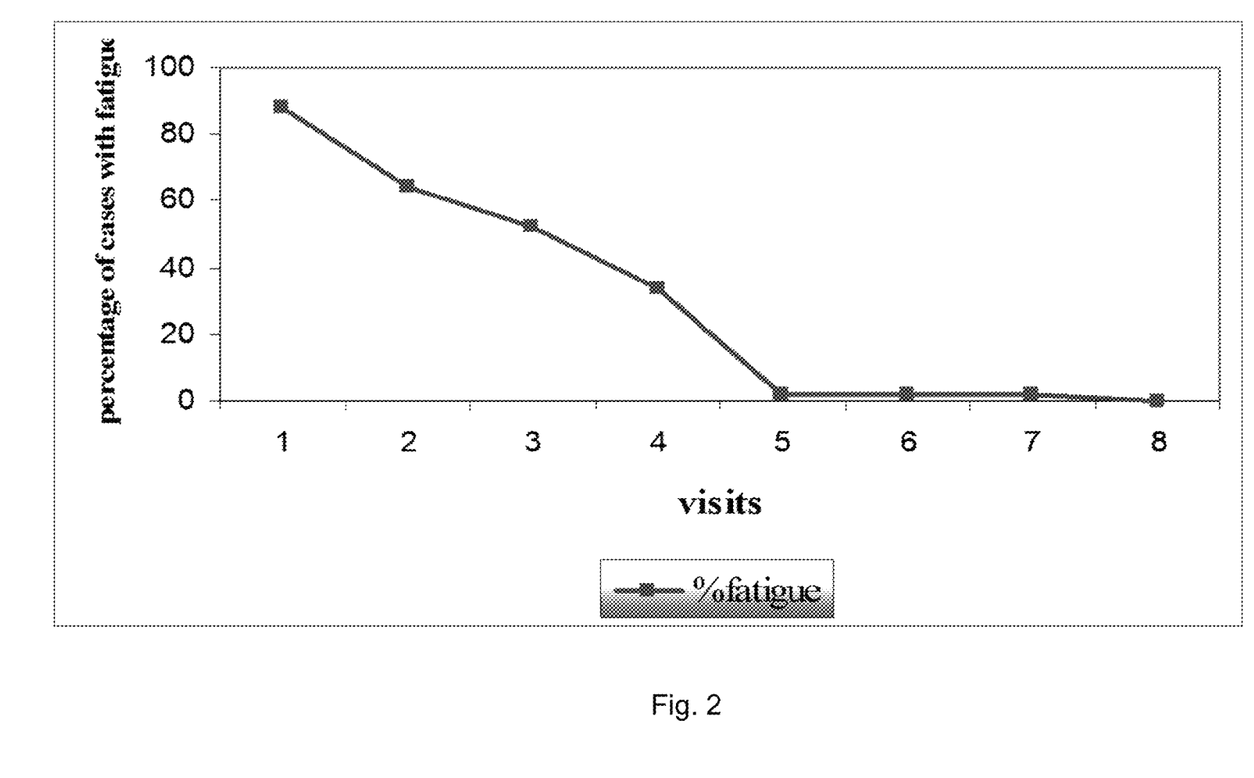
FIG. 2: Percentage of cases with fatigue/malaise after the treatment.

Fatigue/malaise: 88% of the total study cases had symptoms of fatigue at basal. After treatment at the end of $2^{nd}$ week proportion of symptoms of fatigue had a significant fall from basal. After $6^{th}$ week onwards only one or two patients had fatigue (FIG. 2).

Figure 3:
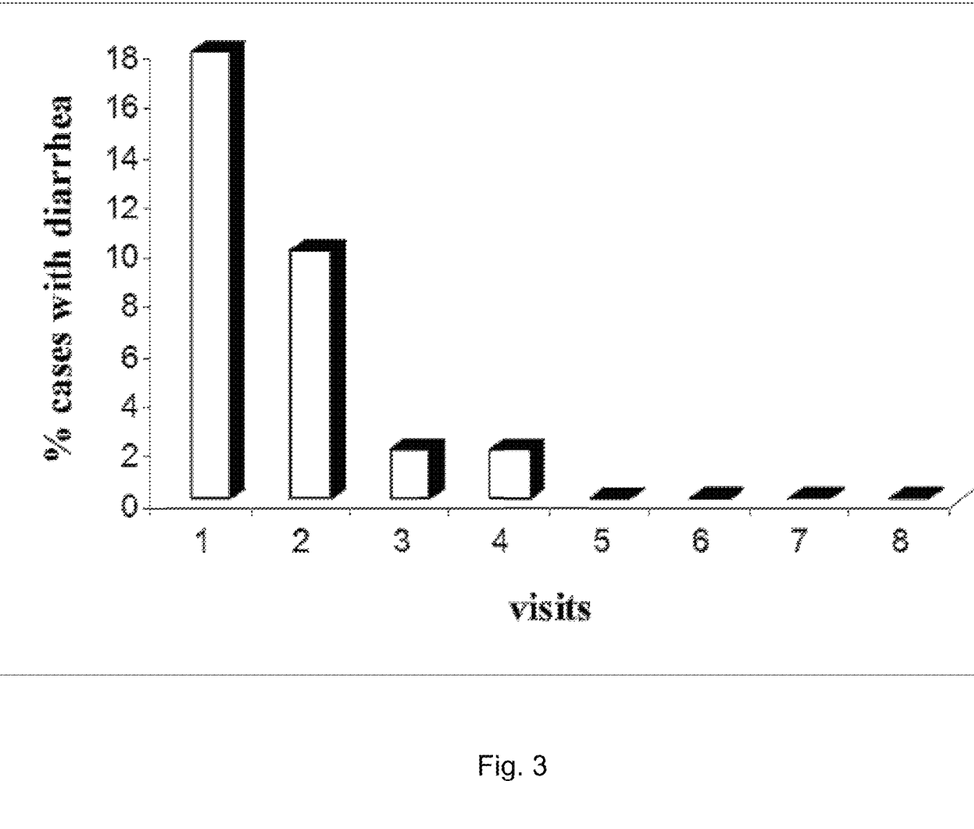
FIG. 3: Percentage of cases with diarrhea after the treatment.

Diarrhea: 18% of the total study cases had diarrhea at basal and after treatment from $5^{th}$ week onwards all the patients had relief from diarrhea (FIG. 3).

Fever: Fever was reported by 24% of total study cases at basal and from $7^{th}$ week onwards not a single patient had fever with significant fall started $4^{th}$ week onwards.

Figure 4:
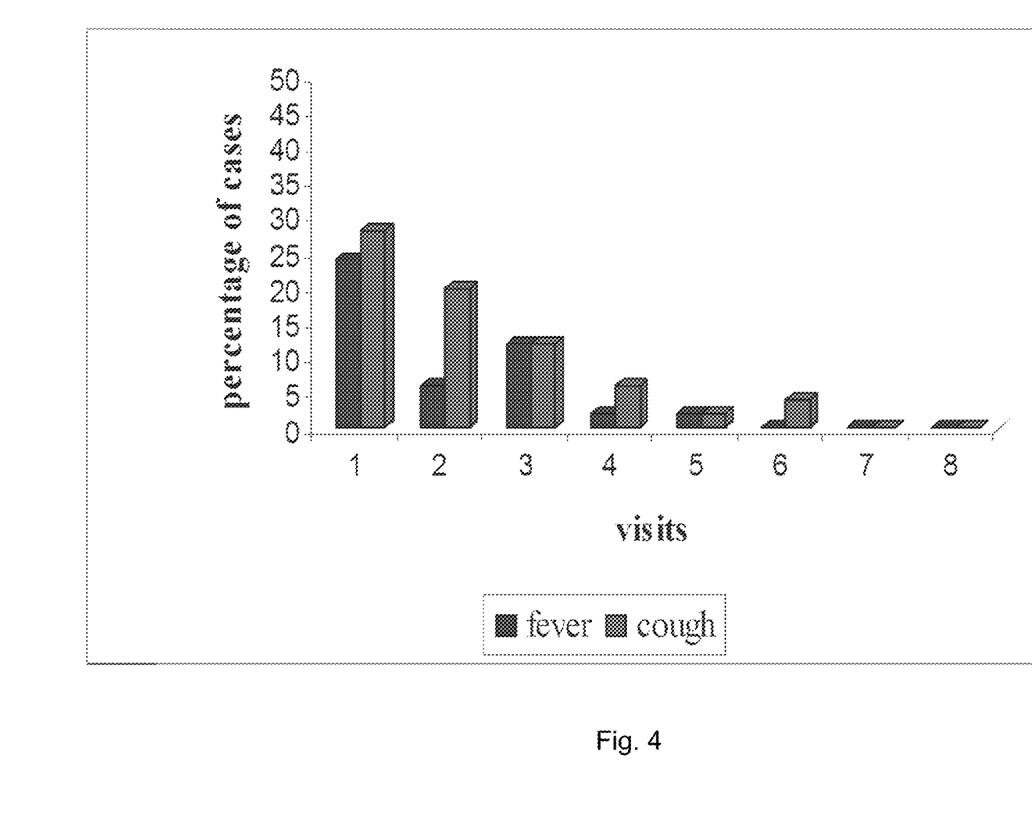
FIG. 4: percentage of cases with fever/cough after therapy.

Cough: 28% of the total study cases had a symptom of cough at basal which had significant fall from $3^{rd}$ week onwards and all improved $10^{th}$ week onward (FIG. 4).

Skin rash and Herpes Zoster: 14% and 12% of total study cases had skin rash and herpes zoster at basal respectively and from $4^{th}$ week onwards not a single patient had suffered from skin rash.

Similarly, nausea, vomiting and disturbed sleep were improved significantly during therapy with formulation of the present invention.

Figure 5:
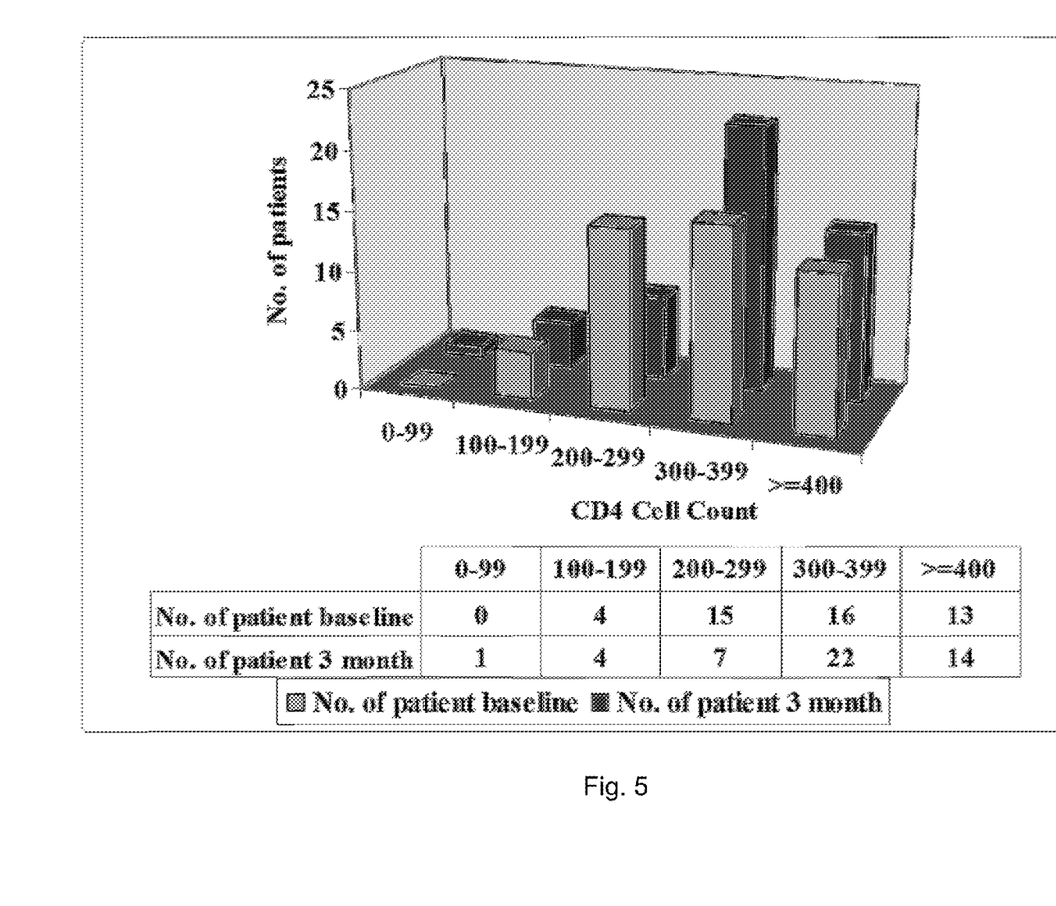
FIG. 5: Number of patients at baseline and at end of treatment with CD4 cell count range.

Absolute CD4 cell count and HIV viral load: CD4 cell count was available for 48 patients with pre and post treatment values. There was increase in CD4 count on the average by 51 (median CD4 cell counts from 312 to 363). This is of borderline statistical significance (p=0.06). 30 out of 48 (62.5%) patients showed rise in CD4 count and 18 patients (37.5%) showed decrease in CD4 cell count. CD4 cell count range with number of patients at baseline and at the end of study is shown in FIG. 5.

The mean HIV log viral load has statistically significantly dropped from 4.63 to 4.18 after 12 weeks of treatment (p=0.03). Similar trend is also seen in the pre treatment and post treatment median viral loads (from 92458 vs. 25332, p<0.001).

Figure 6:
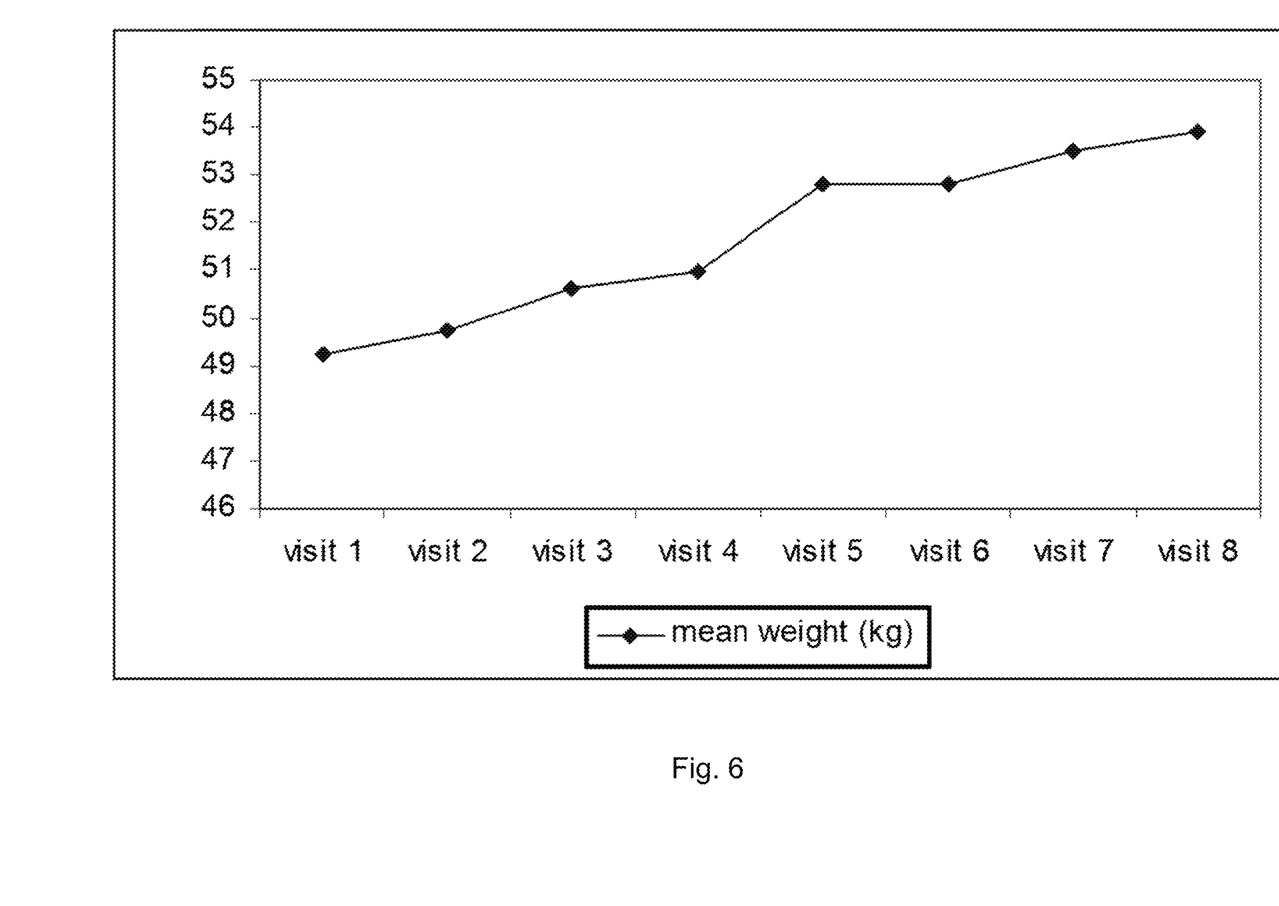
FIG. 6: Mean weight in kg during therapy.

B. Another study was carried out with 51 HIV positive patients by the administration of the formulation comprising peptides of the present invention for twelve weeks. The results obtained are as follows:

Weight gain: Weight monitored on every visit showed significant gain in all 51 HIV patients with mean weight gain of 4.68±1.9 kg after 12 weeks (FIG. 6)

Clinical parameters: All the clinical symptoms had disappeared during the 12 weeks of treatment (most of them had disappeared within 3 weeks). These reductions are statistically significant (p<0.05).

Figure 7:
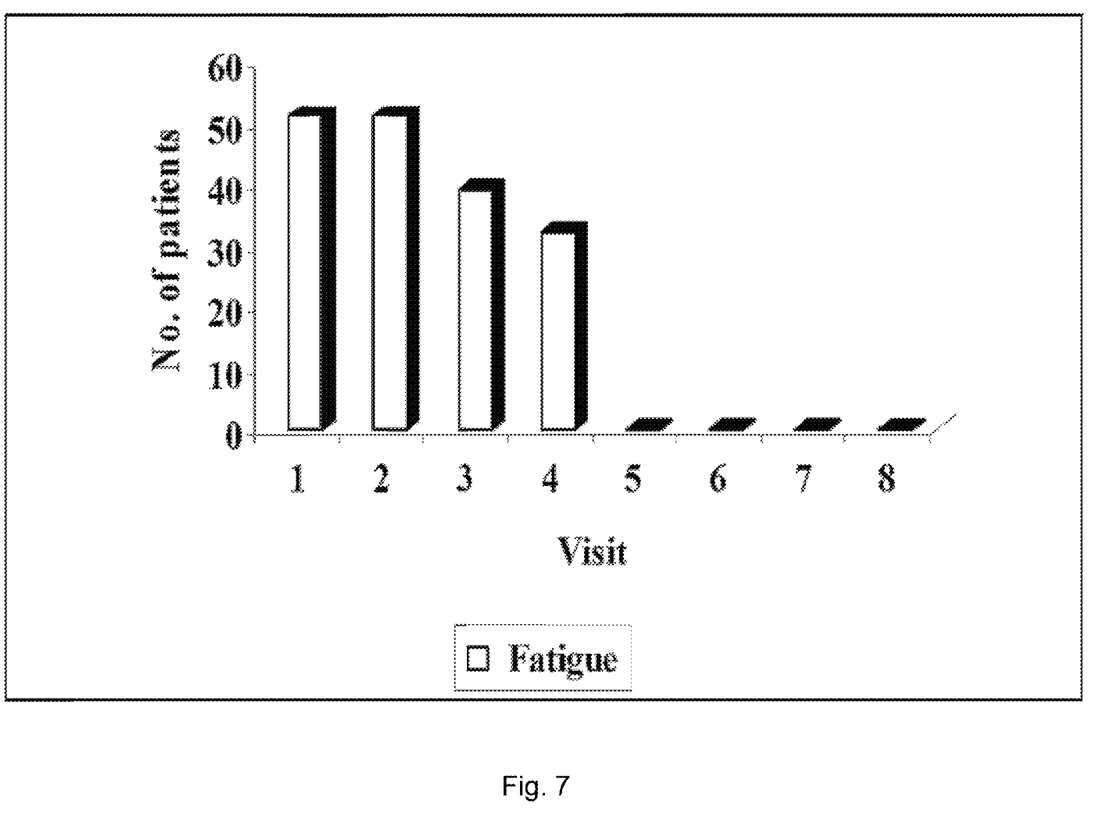
FIG. 7: Number of patients with fatigue/malaise after therapy.

Fatigue/malaise: 100% of the total study cases had symptoms of fatigue at basal. After treatment at the end of $2^{nd}$ week proportion of symptoms of fatigue had a significant fall from basal. After $6^{th}$ week onwards all patients had relief from fatigue (FIG. 7).

Figure 8:
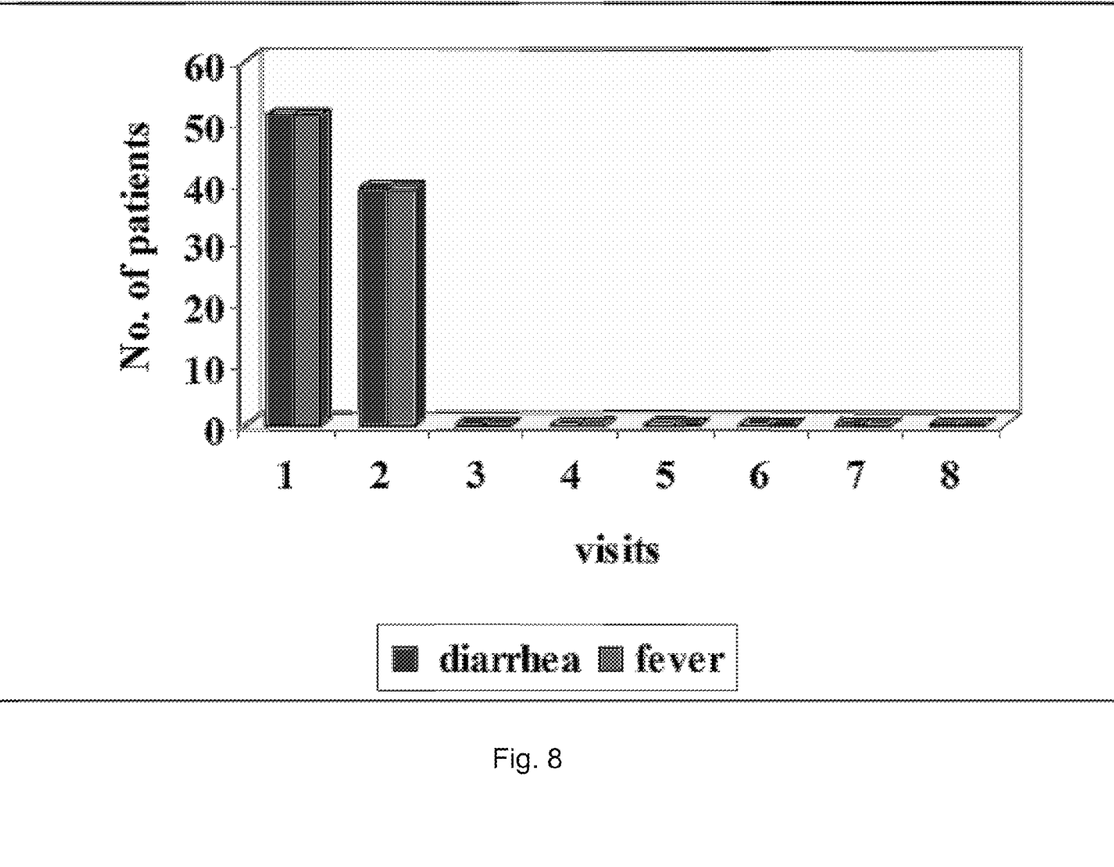
FIG. 8: Number of patients with fever/diarrhea with therapy.

Fever and diarrhea: 100% of the total study cases had fever and diarrhea at basal and after treatment from $3^{rd}$ week onwards. All the patients had relief from diarrhea and fever (FIG. 8).

Figure 9:
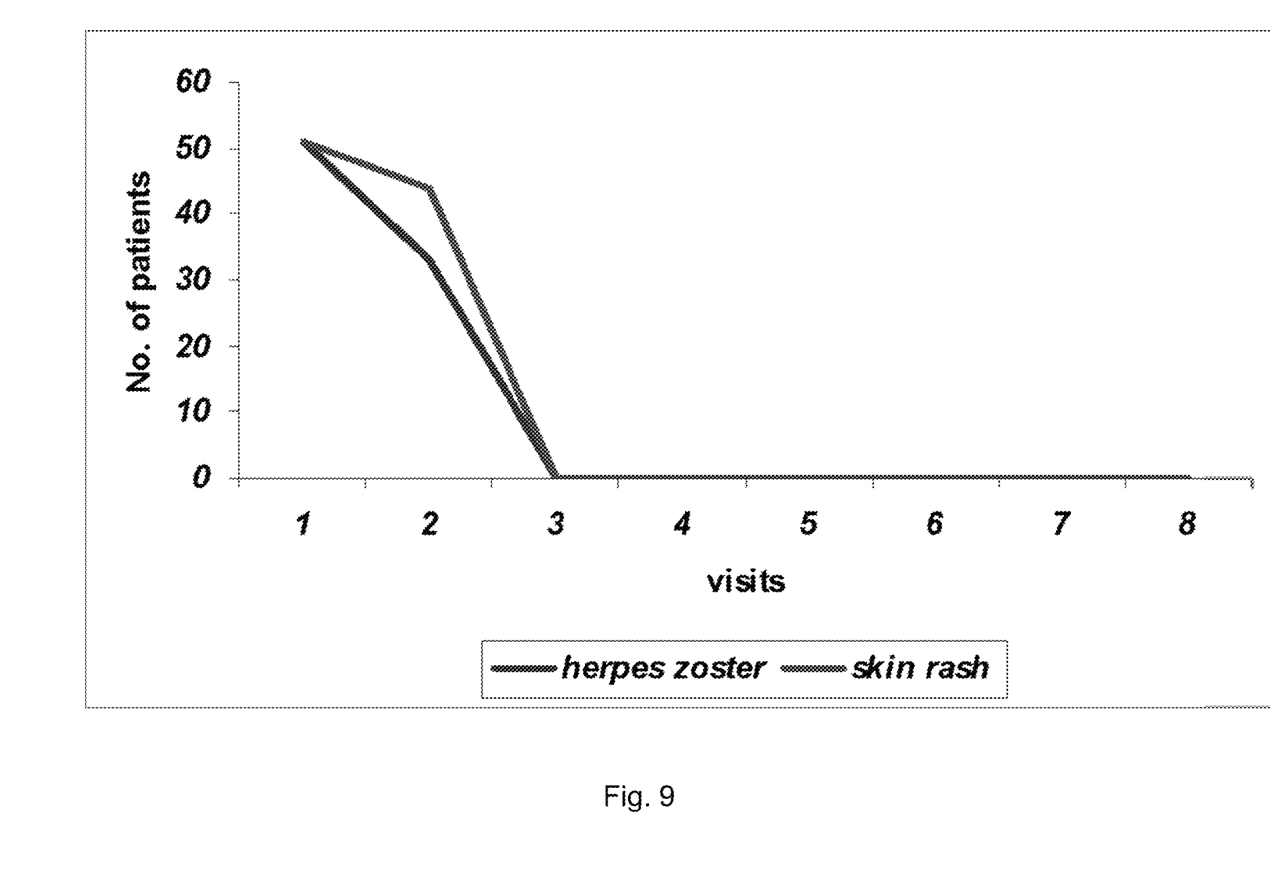
FIG. 9: Number of patients having HIV associated skin rash and herpes zoster after therapy.

Skin rash and Herpes Zoster: All the patients had HIV associated skin rash and herpes zoster at basal and became asymptomatic after $3^{rd}$ week onwards with treatment. (FIG. 9)

Similar improvement seen in nausea, vomiting, cough and disturbed sleep and all patients became asymptomatic from $3^{rd}$ week onwards.

Figure 10:
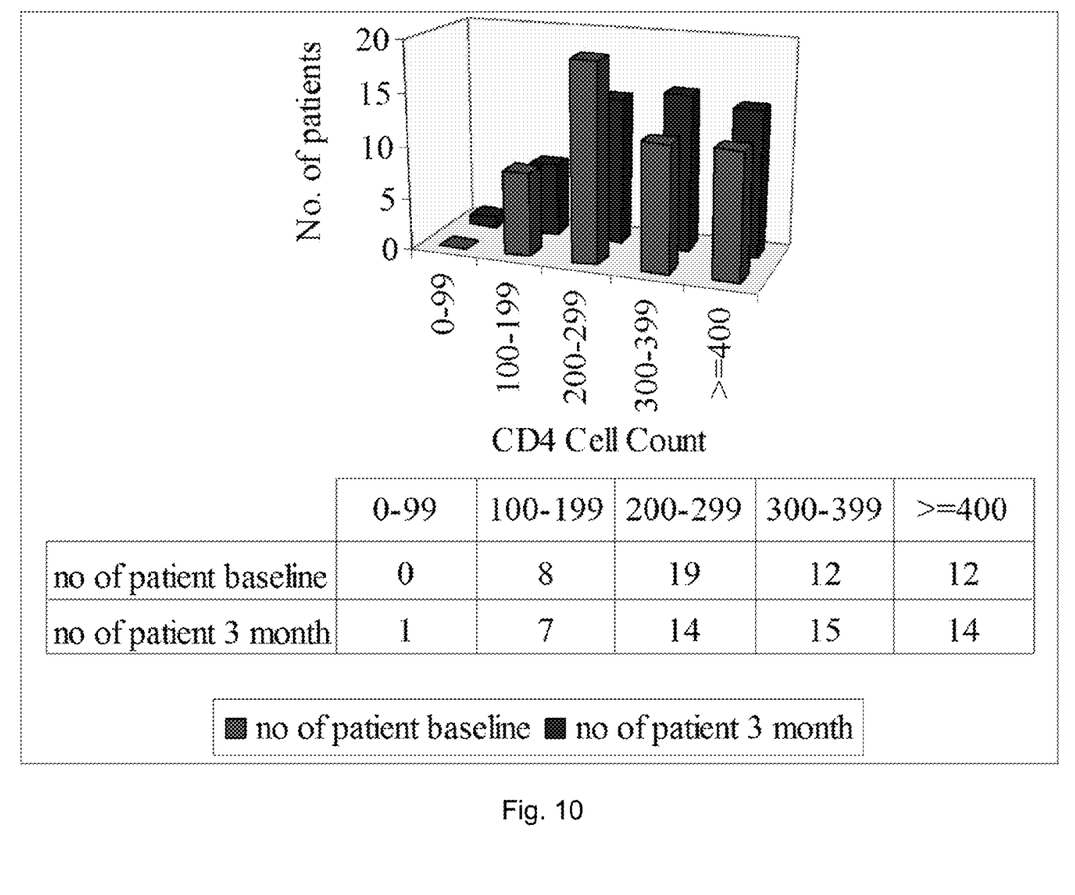
FIG. 10: Number of patients and CD4 cell count range.

Absolute CD4 cell count: CD4 cell count was available for all 51 patients with pre and post treatment values. There was increase in CD4 count on the average by 27 (median CD4 cell counts from 276 to 305). This value is statistically significant (p=0.042). CD4 cell count range with number of patients at baseline and at the end of study is shown in FIG. 10.

HIV viral load: After RADHA108 series 12-week treatment, at the end of study mean viral load showed a significant fall (p<0.001) from the baseline.

Side effects: All patients tolerated the formulation of present invention well with no side effects.

C. The output of the statistical analyses of the study carried out on 50 HIV positive patients is as follows:

| Sr. No. | Parameter | Before | After 12 Weeks | P-value |
|---|---|---|---|---|
| | | I. Physical (N = 50) | | |
| 1. | Weight | 50.48 (10.97) | 55.21 (9.42) | <0.001 |
| | | II. Clinical Symptoms (N = 50) | | |
| 1. | Fatigue | 44 (88%) | 0 (0%) | <0.001 |
| 2. | Diarrhea | 9 (18.0%) | 0 (0%) | 0.004 |
| 3. | Nausea | 8 (16%) | 0 (0%) | 0.008 |
| 4. | Vomiting | 7 (14%) | 0 (0%) | 0.02 |
| 5. | Fever | 12 (24%) | 0 (0%) | <0.001 |
| 6. | Cough | 14 (28%) | 0 (0%) | <0.001 |
| 7. | TB | 6 (12%) | 0 (0%) | 0.03 |
| 8. | Disturbed Sleep | 13 (26%) | 0 (0%) | <0.001 |
| 9. | Rash On Skin | 7 (14%) | 0 (0%) | 0.02 |
| 10. | Herpes Zoster | 6 (12%) | 0 (0%) | 0.03 |
| | | III. Virological | | |
| 1. | Log of HIV-I, RNA n = 34 Median HIV-I RNA $25^{th}$ Percentile $75^{th}$ Percentile | 5.11 (0.090) 206057 62884 508038 | 4.103 (1.32) 25280 1665 87511 | <0.001 <0.001 |
| | | IV. Immunological | | |
| 1. | CD4 count (N = 48) Median $25^{th}$ Percentile $75^{th}$ Percentile | 312.5 275.5 430 | 363.5 294.2 435 | 0.06 |

These results show that formulation containing nano-peptide of the present invention are effective and safe drug in increasing weight and general well being of patients, with decrease in viral load and increase in CD4 cell count. Thus, peptides of the present invention as active pharmaceutical ingredients hold good promise for the treatment of HIV patients across all age groups.

The Radha 108 series peptides of the present invention are active in the treatment of various diseases and conditions as explicated above.

The invention claimed is:

1. A method for treatment of immune related disorders, the method comprising administering a patient suffering from such disorders a therapeutically effective amount of formulation comprising peptides isolated from mammalian colostrum or synthetic peptides of SEQ ID NOS. 1-8, wherein the peptides function to modulate cell immunity and provide attachment inhibition for foreign antigen/viruses on cell surface receptors.

2. The method of claim 1, wherein the immune related disorders are selected from the group consisting of autoimmune disorders, allergies, Alzheimer's, Benign Prostatic Hyperplasia, Cancer, Hypertension, Lupus, Thrush, Autism, Perthes disease, Premenstrual syndrome and Endometriosis, Prion disease, Psoriasis, Sjogren's Syndrome, Spinal Muscular Atrophy, Thrombocytopenia, burns, infection, insect bites, diaper rash, herpetic lesions, Pharangitis, Porphyria, Raynaud's phenomenon, Sarcoidosis, Celiac disease, Chronic Pancytopenia, Crohn's disease, Diabetes type II, Fibromyalgia Rheumatica, Mononucleosis, Multiple Sclerosis, Rheumatoid Arthritis, Osteo Arthritis, Spinal Muscular Atrophy, Brown Recluse Spider Bite, Corneal Regeneration, diarrhea, Guillain Barre Syndrome, Hemolytic Anemia, Idiopathic thrombocytopenic purpura, Myasthenia Gravis, tuberculosis, Human Immunodeficiency Virus (HIV), Hepatitis A and C, Rabies in Dogs, Acute Viral Infections, Dengue fever, Human Pappilloma Virus, Parvo, Rabies, Severe Acute Respiratory Syndrome (SARS), Shingles, Viral Respiratory Infection, Plantar Warts, Cold, Flu, Lymphoma and Herpes Simplex I & II.

3. The method as claimed in claim 2, wherein the immune related disorders are selected from the group consisting of tuberculosis, HIV, Hepatitis A and C, Rabies in Dogs, Acute Viral Infections, Dengue fever, Human Pappilloma Virus, Pharangitis, Rabies, Viral Respiratory Infections, SARS, Cold, Flu, Lymphoma and Herpes Simplex I and II.

4. The method as claimed in claim 2, wherein the immune related disorders are selected from the group consisting of allergies, Alzheimer's, Benign Prostatic Hyperplasia, Cancer, Hypertension, Lupus, Thrush and Autism.

5. The method as claimed in claim 2, wherein the immune relates disorders are selected from the group consisting of Thrombocytopenia and burns.

6. The method as claimed in claim 2, wherein the immune related disorders are selected from the group consisting of Crohn's disease, Diabetes type II, Fibromyalgia, Rheumatica, Mononucleosis, Multiple Sclerosis, Rheumatoid Arthritis, Osteo Arthritis and Spinal Muscular Atrophy.

7. The method as claimed in claim 1, wherein the formulation comprises 0.3% of protein including peptides having SEQ ID NOs. 1-8.

8. The method as claimed in claim 1, wherein the formulation is applied topically, as a skin dermal patch, as a skin spray, as a nasal or intravenous solution.

9. The method as claimed in claimed in 1, wherein the formulation is administered in an amount of 2 ml to 5 ml four times a day.

* * * * *

```
                        SEQUENCE LISTING

<160> NUMBER OF SEQ ID NOS: 8

<210> SEQ ID NO 1
<211> LENGTH: 12
<212> TYPE: PRT
<213> ORGANISM: Bos taurus

<400> SEQUENCE: 1

Glu Leu Val Pro Gly Val Pro Arg Gly Thr Gln Leu
1               5                   10

<210> SEQ ID NO 2
<211> LENGTH: 12
<212> TYPE: PRT
<213> ORGANISM: Bos taurus

<400> SEQUENCE: 2

Val Ala Ile Ile Gln His Met Ile Lys Lys Leu Arg
1               5                   10

<210> SEQ ID NO 3
<211> LENGTH: 13
<212> TYPE: PRT
<213> ORGANISM: Bos taurus

<400> SEQUENCE: 3

Leu Pro Gln Glu Val Leu Asn Glu Asn Leu Leu Arg Phe
1               5                   10

<210> SEQ ID NO 4
<211> LENGTH: 10
<212> TYPE: PRT
<213> ORGANISM: Bos taurus

<400> SEQUENCE: 4

Arg Leu Asn Ala Arg Met Ala Glu Leu Arg
1               5                   10

<210> SEQ ID NO 5
<211> LENGTH: 11
<212> TYPE: PRT
<213> ORGANISM: Homo sapiens

<400> SEQUENCE: 5

Ser Ser Leu Gln Val Leu Asn Met Ser His Asn
1               5                   10

<210> SEQ ID NO 6
<211> LENGTH: 9
<212> TYPE: PRT
<213> ORGANISM: Bos taurus

<400> SEQUENCE: 6

Glu Tyr Gln Glu Leu Met Asn Val Lys
1               5

<210> SEQ ID NO 7
<211> LENGTH: 12
<212> TYPE: PRT
<213> ORGANISM: Bos taurus
```

```
<400> SEQUENCE: 7

Val Asp Thr Leu Asn Asp Glu Ile Asn Phe Leu Arg
1               5                   10

<210> SEQ ID NO 8
<211> LENGTH: 11
<212> TYPE: PRT
<213> ORGANISM: Yaba like disease virus

<400> SEQUENCE: 8

Asp Gly Ile Val Asn Glu Asn Leu Ala Glu Arg
1               5                   10
```